US009618775B2

(12) United States Patent
Salmini

(10) Patent No.: US 9,618,775 B2
(45) Date of Patent: Apr. 11, 2017

(54) DOUBLE-LENS SKI GOGGLES

(75) Inventor: Carlo Salmini, Venice (IT)

(73) Assignee: ANOMALY ACTION SPORTS S.R.L., Mestre (Venice) (IT)

( * ) Notice: Subject to any disclaimer, the term of this patent is extended or adjusted under 35 U.S.C. 154(b) by 0 days.

(21) Appl. No.: 13/812,775

(22) PCT Filed: May 25, 2011

(86) PCT No.: PCT/EP2011/058541
§ 371 (c)(1),
(2), (4) Date: Jan. 28, 2013

(87) PCT Pub. No.: WO2012/013387
PCT Pub. Date: Feb. 2, 2012

(65) Prior Publication Data
US 2013/0128217 A1    May 23, 2013

(30) Foreign Application Priority Data
Jul. 28, 2010    (IT) .............................. VE2010A0046

(51) Int. Cl.
*G02C 11/08*    (2006.01)
*A61F 9/02*    (2006.01)

(52) U.S. Cl.
CPC .............. *G02C 11/08* (2013.01); *A61F 9/028* (2013.01); *A61F 9/025* (2013.01); *A61F 9/027* (2013.01)

(58) Field of Classification Search
CPC .. A61F 9/028; A61F 9/02; A61F 9/022; A61F 9/026; A61F 9/025; A61F 9/027; G02C 11/08; G02C 7/10; G02C 5/00; G02C 2200/16; G02C 3/003; A63B 33/002

USPC .................. 351/62, 63, 44, 41, 156, 81, 43; 2/435–436, 426, 432, 434, 439, 446
See application file for complete search history.

(56) References Cited

U.S. PATENT DOCUMENTS

| 5,428,411 | A  | * | 6/1995 | Kopfer ..................... A61F 9/02 2/436 |
| 6,772,448 | B1 | * | 8/2004 | Hockaday ............... A61F 9/028 2/435 |
| 7,004,580 | B2 | * | 2/2006 | Jackson et al. .................. 351/86 |
| 7,865,977 | B2 | * | 1/2011 | Rayl ....................... A61F 9/028 2/435 |
| 2006/0119948 | A1 | * | 6/2006 | Matsumoto ............... A61F 9/02 359/624 |
| 2006/0272078 | A1 | * | 12/2006 | Polinelli ................. A61F 9/029 2/436 |
| 2008/0055538 | A1 | * | 3/2008 | Kobayashi .............. A61F 9/028 351/62 |

(Continued)

FOREIGN PATENT DOCUMENTS

EP    2044912    4/2009
WO    WO2007085001    7/2007

*Primary Examiner* — Huy K Mai
*Assistant Examiner* — Daniele Manikeu
(74) *Attorney, Agent, or Firm* — Tutunjian & Bitetto, P.C.

(57) ABSTRACT

Ski goggles of the type including a frame of flexible material for supporting an optical system including two mutually facing lenses connected together by a seal gasket which with said lenses forms an air chamber, the gasket being provided with at least one hole which connects the air chamber to the outside and houses a material which is permeable to air but not to water, wherein the gasket forms a cylindrical seat which is filled with said material and communicates with the outside via at least a channel.

3 Claims, 2 Drawing Sheets

(56) References Cited

U.S. PATENT DOCUMENTS

2009/0100577 A1* 4/2009 Kobayashi et al. .............. 2/436
2010/0283956 A1* 11/2010 Jackson et al. ................. 351/49

* cited by examiner

DOUBLE-LENS SKI GOGGLES

TECHNICAL FIELD

The present invention relates to double-lens ski goggles.

DESCRIPTION OF RELATED ART

Ski goggles are known consisting of a flexible rubber frame which adapts to the skier's face and supports a coloured or non-coloured lens.

If used in very cold climates, the lenses tend to mist up as a result of the skier's body or breath temperature during use, especially when the skier is resting.

To prevent the lenses from misting up, it is known to:
subject the lens inner surface to anti-misting chemical treatment, or
provide the optical system with an inner and an outer lens which face each other and are joined together at their perimetral edge by a gasket, to form therebetween an inner space which serves as a heat insulating layer.

These anti-misting treatments present advantages and disadvantages.

The chemical treatment produces an anti-misting effect when the lens has a surface temperature of about 0° C. or higher, but is not satisfactorily effective in an environment in which the surface temperature falls to 0° or lower because the mist forms water droplets which freeze on the lens surface. Moreover, this treatment has little effect at any lens temperature, seeing the low insulating power of plastic having a thickness of just a fraction of a millimetre.

If the optical system comprises two flat lenses (or curved to follow the face profile) and an internal heat insulating space, the lenses are more effective in thermally insulating the goggles, so that the lenses mist up only in more severe circumstances, such as intense perspiration or very cold temperatures.

However these lenses have the drawback that the pressure variation within the internal space between the two lenses, due to atmospheric pressure or temperature change during a descent, deforms the lenses and distorts the visual field. For example, when a lens system is used with the internal space well sealed, a pressure difference arises between the inside and outside of the lenses which subjects the lenses to an overall compressive deformation and distorts the visual field.

To obviate this drawback it has been proposed to perforate one of the two lenses (the inner) and to apply to the hole a diaphragm which is permeable to air but not to water.

However this solution has certain drawbacks, and in particular:
laborious machining with cost increase,
possible damage to the goggles diaphragm during cleaning,
a certain discomfort for the skier due to the presence of the hole with the diaphragm within the visual field,
lens distortion due to the hole made to insert the diaphragm.

SUMMARY OF THE INVENTION

All these drawbacks are eliminated according to the invention by ski goggles as described herein.

BRIEF DESCRIPTION OF THE DRAWINGS

The present invention is further clarified hereinafter with reference to the accompanying drawings, in which.

DETAILED DESCRIPTION OF PREFERRED EMBODIMENTS

Figure 1:
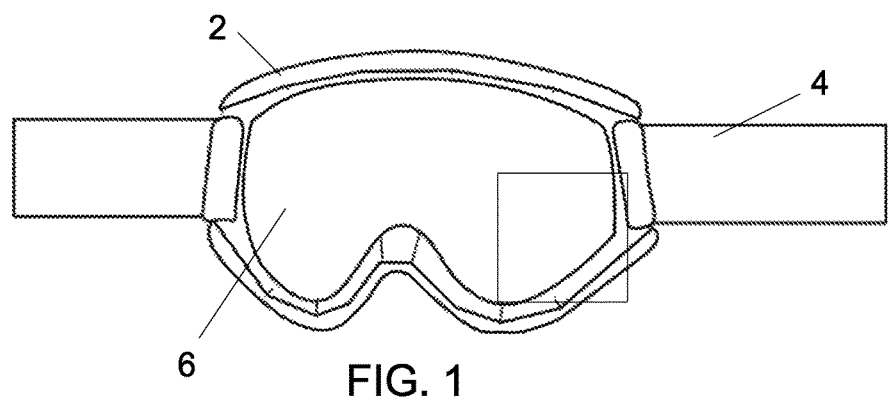
FIG. 1 shows a front view of a pair of ski goggles according to the invention.

As can be seen from the figures, the double-lens goggles according to the invention comprise a masking element 2, an elastic strap 4 connected to the masking element 2, and a lens system 6 removably secured to the masking element 2.

The masking element 2, which is made of soft material such as polyurethane rubber, comprises a perimetral seat for inserting the lens system.

The lens system comprises an inner lens 8 and an outer lens 10, which are of transparent plastic and can be flat or curved, with a specific internal space 12 formed between the two lenses. The internal space serves as a heat insulating layer.

Figure 2:
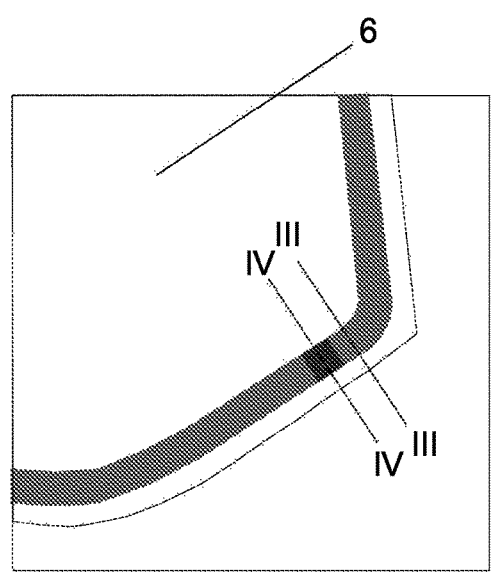
FIG. 2 is a detailed plan view showing the two superposed lenses joined by the gasket.
Figure 3:
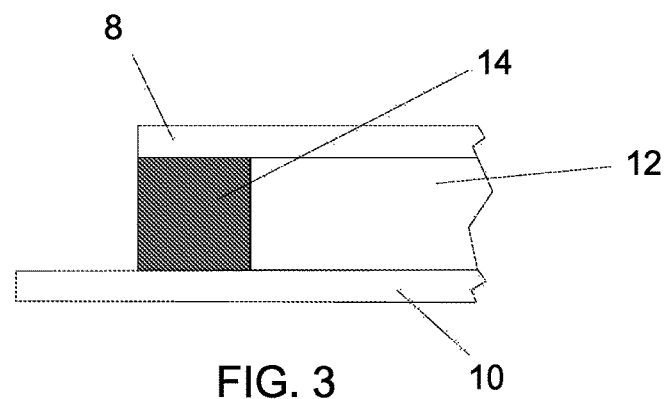
FIG. 3 is a section therethrough on the line of FIG. 2.
Figure 4:
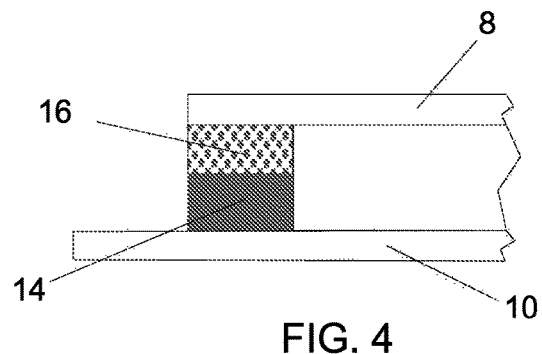
FIG. 4 is a section therethrough on the line IV-IV of FIG. 2.

The two lenses are connected together by a neoprene gasket 14 (FIG. 2) which at certain points, preferably on the low part of the masking element, presents a seat into which a membrane 16 is inserted having the characteristic of allowing air to pass but not water (FIG. 4).

This type of membrane consists of a microporous filter permeable to air but not to water, such as a GORE-TEX® fabric.

Figure 5:
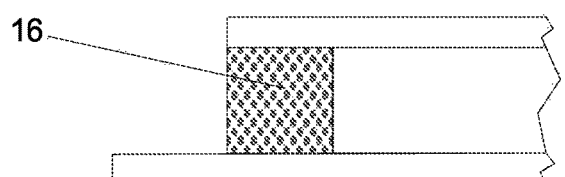
FIG. 5 shows a section through a variant taken on the line IV-IV of FIG. 2.

In a variant, a complete gasket portion 14 is replaced by a layer of membrane 16 (FIG. 5).

Figure 6:
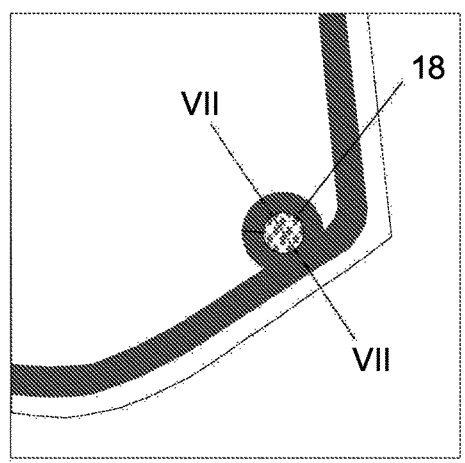
FIG. 6 is a plan view of two superposed lenses using a different system.
Figure 7:
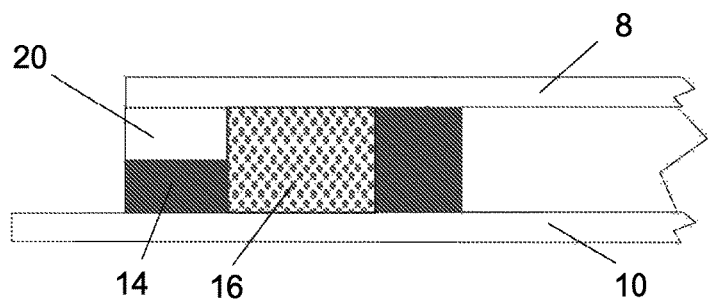
FIG. 7 is a section therethrough on the line VII-VII of FIG. 6.

In the embodiment shown in FIG. 6, the gasket 14 forms a ring 18 defining a cylindrical chamber filled with the membrane 16 of the aforedescribed type.

To enable air to pass through the membrane occupying this chamber, the gasket joining the lenses 8 and 10 can be provided with a cut 20.

The invention claimed is:
1. Ski goggles of the type comprising a frame of flexible material for supporting an optical system consisting of two mutually facing lenses connected together by a seal gasket which with said lenses forms an internal space, the gasket being interposed between said two lenses and shaped to form a ring defining a cylindrical chamber, said cylindrical chamber housing a membrane which is permeable to air but not to water, wherein the gasket includes a first cut to connect the internal space with the cylindrical chamber housing a membrane, and wherein the gasket includes a second cut to connect the cylindrical chamber housing a membrane with the outside.

2. The ski goggles as claimed in claim 1, wherein said membrane comprises a microporous filter permeable to air but not to water.

3. The ski goggles as claimed in any claim 1, wherein said seal gasket is made of neoprene.

* * * * *